US00PP27873P3

(12) United States Plant Patent
Branhagen

(10) Patent No.: US PP27,873 P3
(45) Date of Patent: Apr. 11, 2017

(54) ***CORNUS* PLANT NAMED 'POWELL GARDENS'**

(50) Latin Name: *Cornus obliqua*
Varietal Denomination: Powell Gardens

(71) Applicant: Alan Branhagen, Kingsville, MO (US)

(72) Inventor: Alan Branhagen, Kingsville, MO (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 64 days.

(21) Appl. No.: 14/545,043

(22) Filed: Mar. 19, 2015

(65) Prior Publication Data

US 2016/0278259 P1 Sep. 22, 2016

(51) Int. Cl.
*A01H 5/00* (2006.01)

(52) U.S. Cl.
USPC ..... Plt./220

(58) Field of Classification Search
USPC ..... Plt./220
See application file for complete search history.

(56) References Cited

PUBLICATIONS

UPOV-PLUTO "International Union for the Protection of New Varieties of Plants," Plant Variety Database Jul. 19, 2016, citation for 'Powell Gardens'.*

* cited by examiner

*Primary Examiner* — Susan McCormick Ewoldt
(74) *Attorney, Agent, or Firm* — C. A. Whealy

(57) ABSTRACT

A new and distinct cultivar of *Cornus* plant named 'Powell Gardens', characterized by its upright, outwardly spreading and rounded plant habit; vigorous growth habit; stems that are dark reddish purple in color during the winter; leaves that become dark red purple in color in the autumn; single-type flowers that are white in color; bluish-colored fruits; resistance to stem cankers; and good garden performance.

3 Drawing Sheets

Botanical classification: *Cornus obliqua.*
Cultivar designation: 'POWELL GARDENS'.

BACKGROUND OF THE INVENTION

The present invention relates to a new and distinct cultivar of *Cornus* plant, commercially grown as an ornamental evergreen tree, botanically known as *Cornus obliqua* and hereinafter referred to by the cultivar name 'Powell Gardens'.

The new *Cornus* plant originated from an open-pollination of an unnamed selection of *Cornus obliqua*, not patented, as the female, or seed parent with an unknown selection of *Cornus obliqua*. The new *Cornus* plant was discovered and selected by the Inventor in 1999 as a single plant within the progeny of the stated open-pollination in a controlled environment in Kingsville, Mo.

Asexual reproduction of the new *Cornus* plant by softwood cuttings in a controlled environment in Grand Haven, Mich. since June, 2012 has shown that the unique features of this new *Cornus* plant are stable and reproduced true to type in successive generations.

SUMMARY OF THE INVENTION

Plants of the new *Cornus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Powell Gardens'. These characteristics in combination distinguish 'Powell Gardens' as a new and distinct *Cornus* plant:

1. Upright, outwardly spreading and rounded plant habit.
2. Vigorous growth habit.
3. Stems are dark reddish purple in color during the winter.
4. Leaves that become dark red purple in color in the autumn.
5. Single-type flowers that are white in color.
6. Bluish-colored fruits.
7. Resistance to stem cankers.
8. Good garden performance.

Plants of the new *Cornus* differ primarily from plants of the female parent selection in the following characteristics:

1. Plants of the new *Cornus* are shorter than plants of the female parent selection.
2. Plants of the new *Cornus* and the female parent selection differ in winter stem color as plants of the female parent selection have purple and green-colored stems during the winter.
3. Plants of the new *Cornus* and the female parent selection differ in autumn leaf color as plants of the female parent selection have variable red to purple-colored leaves during the autumn.
4. Plants of the new *Cornus* and the female parent selection differ in flower color as plants of the female parent selection have creamy white to yellowish white-colored flowers.

5. Plants of the new *Cornus* and the female parent selection differ in fruit color as plants of the female parent selection have bluish black-colored fruits.

Plants of the new *Cornus* can be compared to plants of *Cornus sericea* 'Baileyi', not patented. In side-by-side comparisons, plants of the new *Cornus* differed primarily from plants of 'Baileyi' in the following characteristics:

1. Plants of the new *Cornus* were more vigorous than plants of 'Baileyi'.
2. Plants of the new *Cornus* and 'Baileyi' differed in fruit color as plants of 'Baileyi' had white-colored fruits.

Plants of the new *Cornus* can also be compared to plants of *Cornus sericea* 'Ruby', not patented. In side-by-side comparisons, plants of the new *Cornus* differed primarily from plants of 'Ruby' in the following characteristics:

1. Plants of the new *Cornus* and 'Ruby' differed in winter stem color as plants of 'Ruby' had lighter red-colored stems during the winter.
2. Plants of the new *Cornus* and 'Ruby' differed in autumn leaf color as plants of 'Ruby' had variable red-colored leaves during the autumn.
3. Plants of the new *Cornus* and 'Ruby' differed in flower color as plants of 'Ruby' had ivory to creamy white-colored flowers.
4. Plants of the new *Cornus* and 'Ruby' differed in fruit color as plants of 'Ruby' had white-colored fruits.
5. Plants of the new *Cornus* were more resistant to stem cankers than plants of 'Ruby'.

BRIEF DESCRIPTION OF THE PHOTOGRAPHS

The accompanying colored photographs illustrate the overall appearance of the new *Cornus* plant showing the colors as true as it is reasonably possible to obtain in colored reproductions of this type. Colors in the photographs may differ slightly from the color values cited in the detailed botanical description which accurately describe the colors of the new *Cornus* plant.

The photograph on the first sheet is a close-up view of typical leaves of a plant of 'Powell Gardens' grown during the autumn.

The photograph on the second sheet is a close-up view of typical flowers and leaves of a plant of 'Powell Gardens' grown during the spring.

The photograph on the third sheet is a close-up view of typical fruits and leaves of a plant of 'Powell Gardens' during the autumn.

DETAILED BOTANICAL DESCRIPTION

Plants used for the aforementioned photographs and the following observations, measurements and values describe plants grown during the late spring and autumn in three-gallon containers and ground beds in a polypropylene-covered shadehouse in Grand Haven, Mich. and under cultural practices typical of commercial *Cornus* production. During the production of the plants, day temperatures ranged from 18° C. to 27° C. and night temperatures ranged from ranged from 5° C. to 10° C. Plants were two years old when the photographs and description was taken. In the following description, color references are made to The Royal Horticultural Society Colour Chart, 1995 Edition, except where general terms of ordinary dictionary significance are used.

Botanical classification: *Cornus obliqua* 'Powell Gardens'.

Parentage:

*Female, or seed, parent*.—Unnamed selection of *Cornus obliqua*, not patented.

*Male, or pollen, parent*.—Unknown selection of *Cornus obliqua*, not patented.

Propagation information:

*Type*.—By softwood cuttings.

*Time to initiate roots, summer*.—About one month at temperatures about 20° C.

*Time to produce a rooted young plant, summer*.—About four months at temperatures about 20° C.

*Root description*.—Fine to medium in thickness; creamy white to brown in color.

*Rooting habit*.—Freely branching; dense.

Plant description:

*Plant form and growth habit*.—Upright, outwardly spreading and rounded perennial shrub; vigorous growth habit; rapid growth rate.

*Plant height*.—About 54 cm.

*Plant width (spread)*.—About 50.5 cm.

*Lateral branches*.—Aspect: Erect to about 45° from vertical. Length: About 54 cm. Diameter: About 4 mm. Internode length: About 5.3 cm. Strength: Strong. Texture: Slightly pubescent. Color, developing branches: Close to 146B. Color, mature branches: Close to 144A heavily speckled with close to 177A and 177B; in the winter, color becoming closer to 183A.

Leaf description:

*Arrangement*.—Opposite, simple.

*Length*.—About 7 cm.

*Width*.—About 3 cm.

*Shape*.—Lanceolate.

*Apex*.—Acute.

*Base*.—Cuneate.

*Margin*.—Entire.

*Texture, upper surface*.—Smooth, glabrous.

*Texture, lower surface*.—Slightly pubescent; slightly rough.

*Venation pattern*.—Pinnate.

*Color, spring and summer*.—Developing and fully developed leaves, upper surface: Close to 137A; venation, close to 145A. Developing and fully developed leaves, lower surface: Close to 138B; venation, close to 145C.

*Color, autumn*.—Fully developed leaves, upper surface: Close to 71A; venation, close to 60C and 145A. Fully developed leaves, lower surface: Close to 138B; venation, close to 145C.

*Petioles*.—Length: About 1 cm. Diameter: About 1.5 mm. Texture, upper surface: Smooth, glabrous. Texture, lower surface: Pubescent; slightly rough. Color, upper surface: Close to 145A. Color, lower surface: Close to 145C.

Flower description:

*Flower appearance and arrangement*.—Upright rotate flowers arranged in corymbs; about 27 flowers per inflorescence; flowers face mostly upright.

*Natural flowering season and flower longevity*.—Plants flower during the spring in Michigan; flowers not persistent.

*Fragrance*.—None detected.

*Inflorescence diameter*.—About 8 cm.

*Inflorescence height*.—About 4 cm.

*Flower diameter*.—About 1 cm.

*Flower length*.—About 1 cm.

*Flower buds*.—Length: About 9 mm. Diameter: About 4 mm. Shape: Ovate to oblong. Color: Close to 150C and 150D.

*Petals*.—Quantity and arrangement: Four in a single whorl. Length: About 5 mm. Width: About 2 mm. Shape: Lanceolate. Apex: Acute. Base: Cuneate. Margin: Entire. Texture, upper and lower surfaces: Smooth, glabrous. Color: When opening, upper and lower surfaces: Close to 155D. Fully opened, upper and lower surfaces: Close to 155D.

*Sepals*.—Quantity and arrangement: Four in a single whorl. Length: About 1 mm. Diameter: About 0.5 mm. Shape: Lanceolate to narrowly deltoid. Apex: Acute. Base: Truncate. Margin: Entire. Texture, upper and lower surfaces: Smooth, glabrous. Color: When opening, upper and lower surfaces: Close to 145B. Fully opened, upper and lower surfaces: Close to 145B.

*Peduncles*.—Length: About 6.5 cm. Diameter: About 2 mm. Aspect: Upright to about 30° from vertical. Strength: Strong. Texture: Slightly pubescent. Color: Close to 145A and 185A.

*Pedicels*.—Length: About 5 mm. Diameter: About 1 mm. Aspect: Upright to about 35° from vertical. Strength: Strong. Texture: Slightly pubescent. Color: Close to 185C.

*Reproductive organs*.—Androecium: Quantity per flower: About four. Filament length: About 2 mm. Filament color: Close to 155C. Anther length: About 1 mm. Anther shape: Round. Anther color: Close to 199C. Pollen amount: None observed. Gynoecium: Quantity per flower: One. Pistil length: Less than 1 mm. Style length: Less than 1 mm. Style color: Close to 155C. Stigma shape: Cylindrical. Stigma color: Close to 155C.

*Fruits*.—Length: About 1 cm. Diameter: About 8 mm. Texture: Smooth. Color: Initially, close to 145B with occasional spots, close to 144A; with development, closer to 144D overlain with close to 189B and 103C; fully developed, close to 103C.

Disease & pest resistance: Plants of the new *Cornus* have been observed to be resistant to stem canker pathogens common to *Cornus* plants. Plants of the new *Cornus* have not been observed to be resistant to pests and other pathogens common to *Cornus* plants.

Garden performance: Plants of the new *Cornus* have been observed to have good garden performance and to be tolerant to wind, rain, drought, high temperatures about 40° C. and low temperatures about −26° C.

It is claimed:

1. A new and distinct *Cornus* plant named 'Powell Gardens' as illustrated and described.

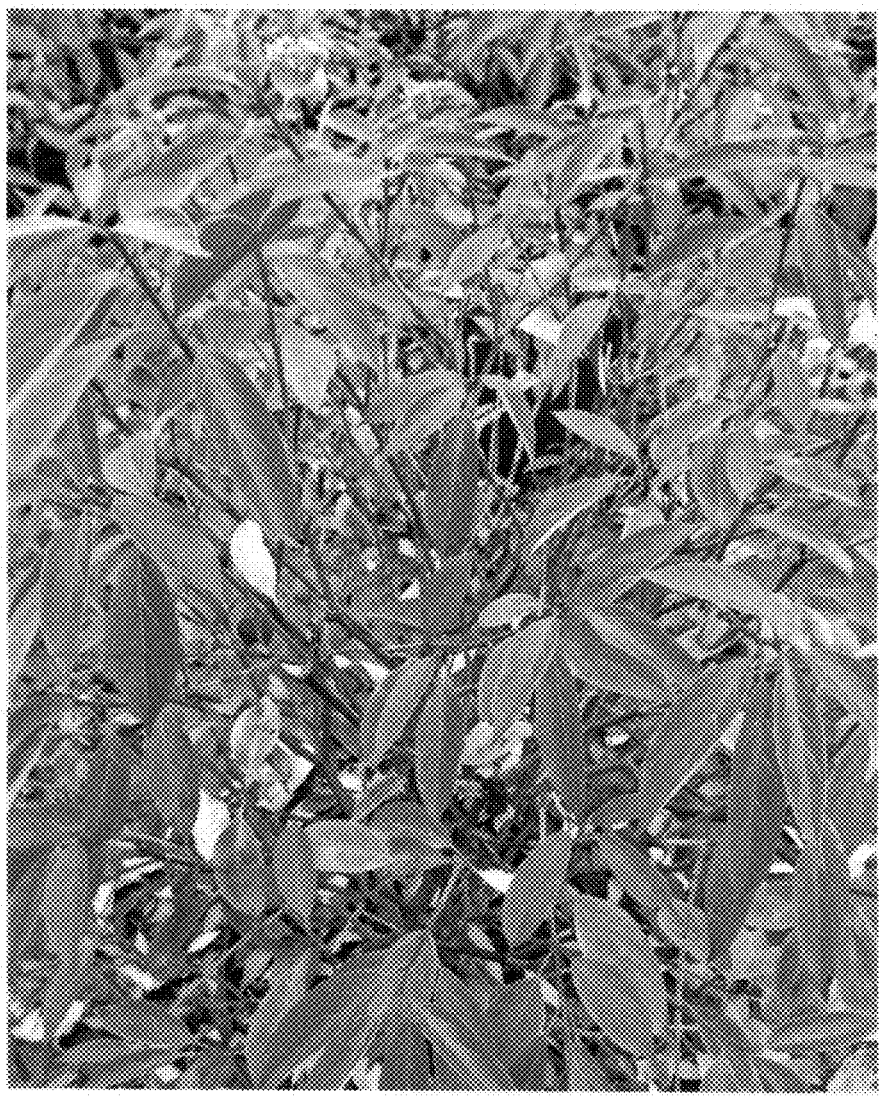

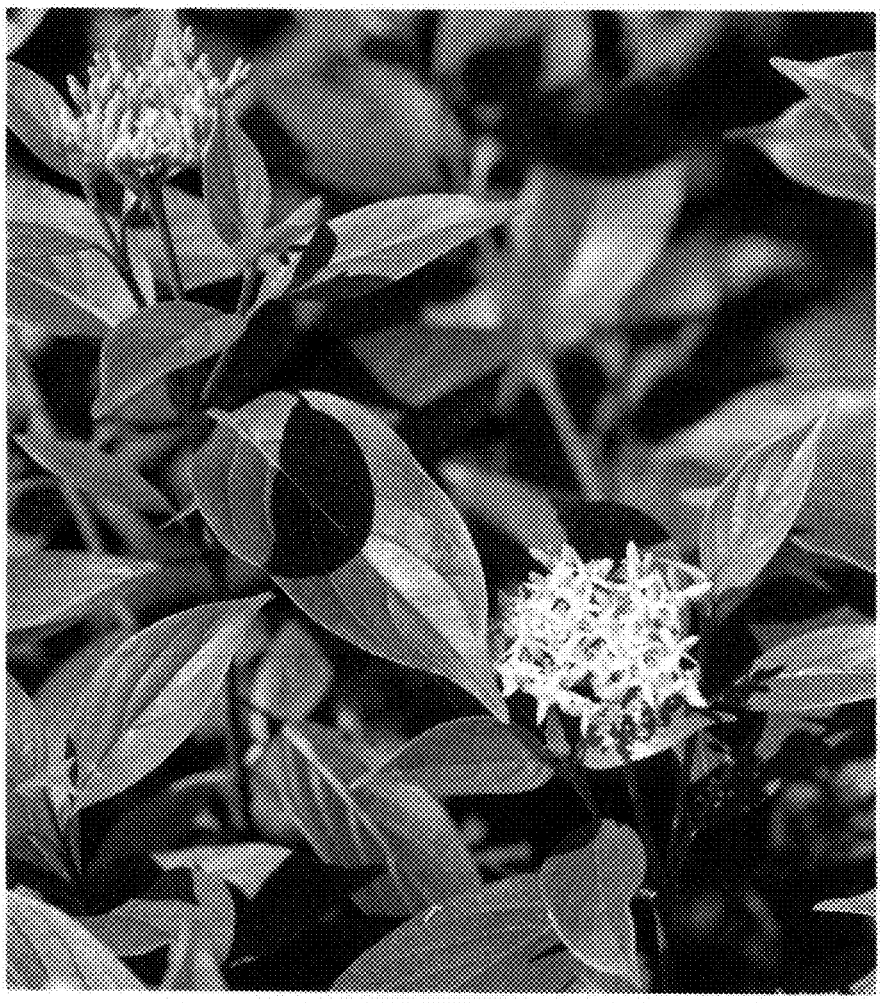

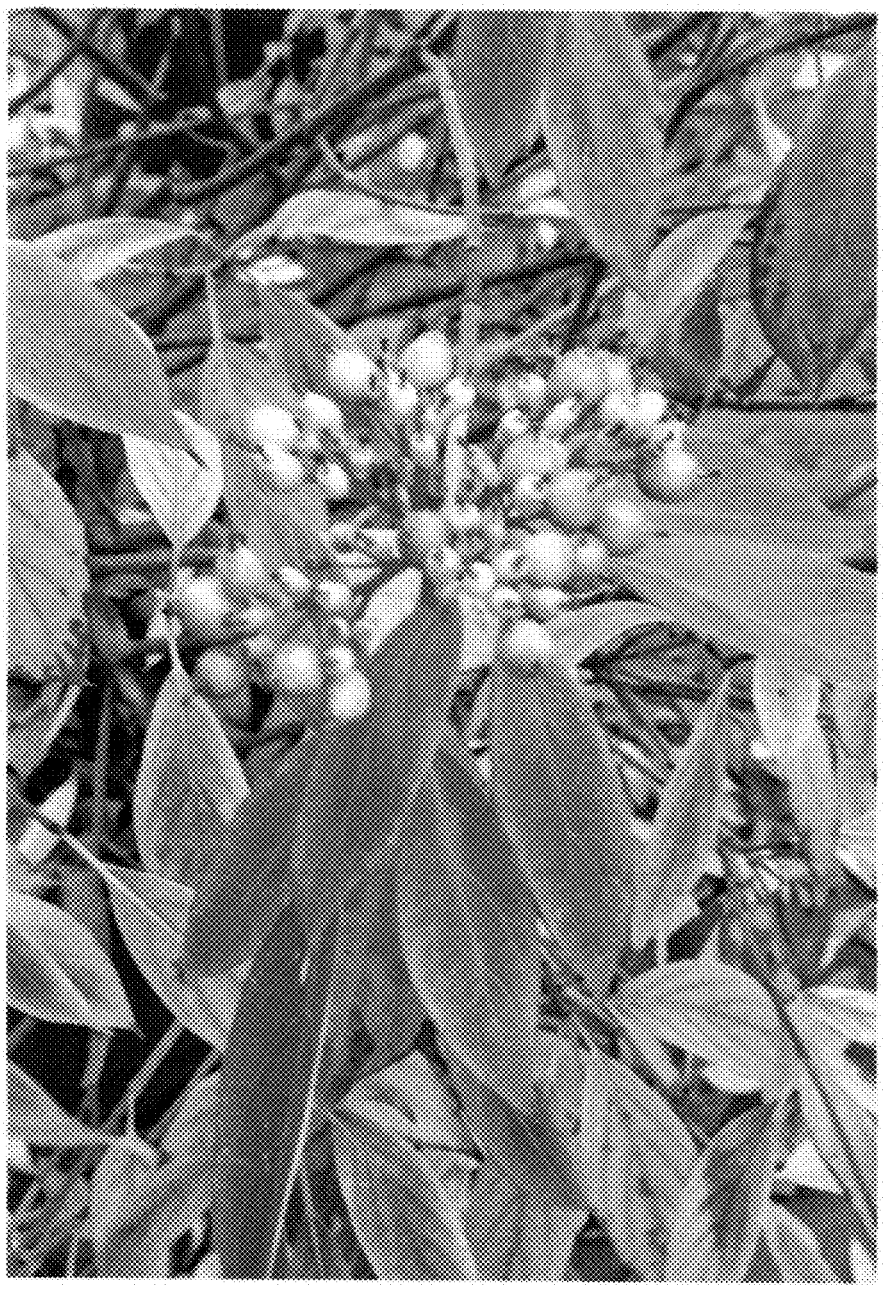

* * * * *